United States Patent
Shelton

(10) Patent No.: US 7,028,049 B1
(45) Date of Patent: Apr. 11, 2006

(54) STANDING ORDER DATABASE SEARCH SYSTEM AND METHOD FOR INTERNET AND INTERNET APPLICATION

(75) Inventor: Robert H. Shelton, Irvine, CA (US)

(73) Assignee: Allcare Health Management System, Inc., Ft. Worth, TX (US)

( * ) Notice: Subject to any disclaimer, the term of this patent is extended or adjusted under 35 U.S.C. 154(b) by 1207 days.

(21) Appl. No.: 09/025,279

(22) Filed: Feb. 18, 1998

Related U.S. Application Data

(60) Provisional application No. 60/037,869, filed on Feb. 17, 1996, now abandoned.

(51) Int. Cl.
*G06F 17/30* (2006.01)

(52) U.S. Cl. ............................................. 707/104.1; 1/9
(58) Field of Classification Search ............... 707/1–10, 707/100–104.1, 200–206; 705/2–3, 4; 709/225; 713/200–202
See application file for complete search history.

(56) References Cited

U.S. PATENT DOCUMENTS

| | | | | |
|---|---|---|---|---|
| 3,872,448 A | * | 3/1975 | Mitchell, Jr. .................... | 705/3 |
| 5,361,202 A | * | 11/1994 | Doue ............................. | 705/3 |
| 5,673,316 A | * | 9/1997 | Auerbach et al. ............... | 705/5 |
| 5,924,074 A | * | 7/1999 | Evans ............................ | 705/3 |
| 5,943,423 A | * | 8/1999 | Muftic .......................... | 707/67 |

OTHER PUBLICATIONS

Anderson R. J., A security policy model for clinical information system, Security and Privacy, 1996., Procedings., 1996 Symposium on, pp. 30-43.*

National Library of Medicine, Confidentiality of Electronic Health Data (CBM 95-10); Last updated: Dec. 31, 1996 (40 pages).

* cited by examiner

*Primary Examiner*—John Breene
*Assistant Examiner*—Jean Bolte Fleurantin
(74) *Attorney, Agent, or Firm*—Thomas, Kayden, Horstemeyer & Risley LLP

(57) ABSTRACT

An internet and/or intranet based database search system and method for conducting searches of highly confidential records such as individual patient medical records and to automate the process of securing required approvals to make such records available to a properly authorized and authenticated requesting party. The system's central premise is that the patient has a fundamental right to the confidentiality of their personal medical records and should control that right through specific, informed consent each time that a party requests to receive them. It reinforces the widely held conception of privacy in general as well as of the sanctity of the doctor/patient relationship by granting the doctor the right, subject to the patient's express permission, to initiate a search request. At the same time, it provides an expedited and cost-efficient means for transfer of such records as demanded by many healthcare reform proposals and gives the repositories where these records are held the right to stipulate the specific terms and conditions that must be fulfilled before they will release documents entrusted to their care, thereby substantially reducing the risk of litigation alleging breaches of patient confidentiality. And it carries out all of these legitimate interests in a way that is fast, simple to use and easy to audit. The system optionally includes a billing mechanism to pay for any added cost associated with providing this additional protection; and in its preferred embodiment, is applicable to both digital as well as non-digital records.

81 Claims, 6 Drawing Sheets

STANDING ORDER DATABASE SEARCH SYSTEM AND METHOD FOR INTERNET AND INTERNET APPLICATION

CROSS REFERENCES TO RELATED APPLICATION

This application claims the benefit of prior filed U.S. Provisional Patent Application, No. 60/037,869, filed Feb. 17, 1996 now abandoned.

BACKGROUND OF THE INVENTION

This invention relates generally to the field of transmission of medical records, and more particularly to a standing order database search system and method for such transmission having Internet and intranet application.

In a recent Harris poll, 85% of respondents said they believe protecting the confidentiality of medical records is "absolutely essential" or "very important" within healthcare reform. As this survey result suggests, people are concerned about the risks powerful, new information technologies could pose to their rights of privacy. In an ironic way, the inefficiencies of the past have served as something of a comfort—despite the fact that more than a quarter of Americans responding to a 1993 Harris poll said health information about them had been improperly disclosed in the past.

Reflecting the inadequacy of a technological solution to the issue, various leaders have sought a political resolution. In 1995, Senator Robert Bennett (R-Utah) introduced the so-called Medical Confidentiality Act of 1995. Although the legislation remains mired in debate, one thing has become clear from remarks made by both the staunch advocates for the legislation as well as its numerous dissenting voices, most of which feel that its protections are inadequate. This fact is that comprehensive protection must be devised to guarantee the confidentiality and integrity of computer-based patient records as well as the data networks to carry such information.

None of the prior technologies has been able to strike this balance between protecting confidentiality and facilitating the transfer of individual medical records. The San Jose Mercury News, a widely recognized online resource for Silicon Valley companies reported the following headline in its Mar. 4, 1997 edition: "The electronic privacy issue is shaping up as a major-league battle in the 105th Congress." On Mar. 5, 1997, Wired Magazine reported in a story entitled "Panel Urges Medical Data Protection" as follows: "Right now, if your medical records are on a computerized database or are transmitted, you run the risk of having them seen by people you never dreamed would be perusing your health information."

The deficiency in prior technology to deliver the combined benefit of adequate protection of confidentiality and support for an ubiquitous, easy-to-deploy and use, and cost-effective means for the transfer of medical records is perhaps best noted in the written and oral testimony before various Congressional committees debating privacy legislation.

During his Jan. 13, 1997 opening remarks before the National Committee on Vital Health Statistics, Subcommittee on Privacy and Confidentiality, Dr. Robert Gellman, a privacy and information policy consultant in Washington and the subcommittee chair stated: "We intend to cover the full range of fair information practices issues, including patient's rights, limits on use and disclosure of information, health identification numbers, pre-emption of state laws and privacy-enhancing technologies when available, sometimes known as PETs—privacy-enhancing technologies."

The subcommittee's first witness, Dr. David Korn, Professor of Pathology, and immediate past Vice President of Stanford University, Dean of the Stanford Medical School and a distinguished scholar in residence at the AAMC, stated: "The difficult challenge before this committee is to find a point of balance that will enable to us to enhance the security of confidential medical information and reduce the probability of its misuse, without substantially impairing the access and communication that are essential to the effective delivery of medical care, the efficient functioning of the health care delivery system and the pace of biomedical and health services research." Dr. Korn concluded his remarks by stating, in part, "[G]iven the requirements for access and communication in the real worlds of medical care and biomedical research, such levels of security in my judgment are fanciful."

On Feb. 3, 1997, David L. Larsen, Director of Health Care Services at Salt Lake City-based Intermountain Health Care (IHC), testified on behalf of the American Association of Health Plans (AAHP) which represents 1,000 HMOs, PPOs, and similar network plans providing care to over 120 million Americans. In his testimony, Mr. Larsen stated: "AAHP supports this Committee's efforts to protect against the unauthorized and inappropriate use of patient information while at the same time facilitate the coordination and delivery of high quality, network-based health care. It is important that your recommendations recognize the special needs of integrated delivery systems.

"In order to manage and improve the health outcomes of the population we insure, we must be able to share information among IHC corporate entities—our physicians, hospitals, and health plans. IHC has developed electronic medical records and common databases to facilitate this communication. Preventing the creation of these common databases, limiting the type of data which can be shared within the IHC integrated delivery system, or requiring a patient's authorization for each and every transaction and transfer of data, would severely limit IHC's ability to measure and improve the health outcomes of our enrollees."

Robert B. Burleigh, President of Brandywine Healthcare Services and Consultant to the Board of Directors of the International Billing Association (IBA), the only trade association representing third party medical billing companies, also testified before the National Committee on Vital and Health Statistics Subcommittee on Privacy and Confidentiality on Feb. 3, 1997. In his testimony, Mr. Burleigh stated: "[Section 111 (d) of the proposed legislation] provides that a 'health information trustee may disclose protected health information only if the recipient has been notified that the information is protected health information . . . ' In the normal course of business today, the technical means of notifying a recipient of (proposed) protected health information, prior to, or concurrently with, disclosure does not exist."

Mr. Burleigh concluded his testimony with the following warning: "We are concerned that an unintended result of this proposed legislation would be the decision by providers to discontinue accepting insurance coverage in order to avoid the burdensome (in their view) new duties of securing informed consents, providing disclosures, maintaining new disclosure logs and related records, and other proposed responsibilities."

On February 18, Lauren Dame, staff attorney at Public Citizen's Health Research Group, a non-profit organization founded in 1971 by Ralph Nader and Dr. Sidney Wolfe, testified before the committee. In her prepared remarks, Ms. Dame stated: "As medical records are computerized and there is increased disclosure of sensitive medical information—as we believe there will be—many of the problems consumers face today will be exacerbated unless strong privacy protections are included in any regulations developed . . . [P]rivacy for medical information is an important value in and of itself. People feel very strongly that they should have control over the dissemination of what amounts to highly intimate and private information about themselves.

"[W]e believe that any effort to regulate the use and development of computerized patient medical records should begin with the proposition that . . . personally identifiable patient information should not be disclosed without the informed consent of the patient. (And, by "informed consent", I do not mean the kinds of blanket consent or release forms patients currently are forced to sign in order to obtain health insurance, which basically give the insurers the right to collect any medical information they want, and to do with it what they will.)"

Ms. Dame concluded her remarks with this statement which indicates the solutions have yet to be devised: "[Y]ou have heard from insurers, providers, and processors of data, and no doubt most of them have painted glowing pictures of the great increases in efficiency and cost savings associated with computerizing medical records and with limiting privacy protections. While in some areas, the interests of all of us might be accommodated, often you will be faced with some hard choices . . . In making your recommendations to the Secretary, I urge you to err on the side of protecting the privacy and confidentiality of personally-identifiable medical information. As a society, we can always modify regulations to increase data exchange if experience shows us that we can safely do so. But privacy, once lost, cannot be recaptured."

On Feb. 19, 1997, Dr. Denise Nagel, a physician, instructor at Harvard Medical School and co-founder of the National Coalition for Patient Rights, an organization whose mission is to protect and preserve privacy and confidentiality in medical care, testified for that organization and on behalf of the American Psychoanalytic Association and the Association of American Physicians and Surgeons. During her testimony, Dr. Nagel quoted the 1996 Time/CNN poll which "found that 87% of Americans believed that 'laws should be passed that prohibit health care organizations from giving out medical information without first obtaining the patient's permission.'" and commented that "the same percentage of people in a 1993 Louis Harris poll trusted their own providers but most (71%) believed that 'if privacy is to be preserved, the use of computers must be sharply restricted in the future.'" Dr. Nagel stated her opinion: "Rules that conform to these views would require consent for placing personal information in a computer system and consent for the disclosure of identified information, except in rare circumstances."

Merging these two fiercely advocated perspectives—efficiency of a system for delivering records and informed consent—into a single system is one of the essential missing features of the prior art.

SUMMARY OF THE INVENTION

The primary object of the invention is to better protect the confidentiality of medical records.

Briefly, the present invention comprises a medical data base supervisory control system comprising:

(a) at least one data base including medical data individually relating to each of a plurality of patients, (b) internet and/or intranet means for requesting and accessing said medical data, (c) means for identifying medical data for each of said patients with conditions required for accessing of said medical data, and (d) data processing means for comparing said request with said conditions required for access of said data and, when said request fails to comply with said conditions, for denying access to said data.

The invention also comprises a method of controlling access to medical data in a medical data bases comprising:

(a) maintaining at least one data base including medical data individually relating to each of a plurality of patients, (b) identifying medical data for each of said patients with indicia indicative of conditions required for access of said medical data, (c) selectively introducing internet and/or intranet requests for access to said data, and (d) comparing said requests with said conditions; and, when said requests fail to comply with said conditions, automatically denying access to said data.

OBJECTS AND FEATURES OF THE INVENTION

One general object of the invention is to provide an opportunity for the informed consent by the patient for such records to be made available to healthcare providers and trustees, such as payers, auditors, and the like.

Another object of the invention is to assist doctors, hospitals, and other healthcare providers, as well as to health insurance payors assess whether a procedure recommended by a health care provider is one that should be covered by the insurance.

A further object of the invention is to simplify the process of securing second opinions.

Yet another object of the invention is to reduce the time involved in transmitting medical data from one health care provider to another and thereby to ensure prompt patient treatment and care.

Still yet another object of the invention is to automate the process of securing required approvals to make a patient's personal medical records available to a medical service provider such as a doctor or hospital.

Another object of the invention is to provide a fully integrated system and method for conducting searches of data bases while protecting the privacy of such data bases, particularly of medical data bases by health care providers.

Another object of the invention is to provide automated approval for access to a data base of confidential records and transmission of data therefrom once appropriate approval is received.

A further object of the invention is to provide for patient approval of access to medical records in data bases.

Yet another object of the invention is to permit health care providers to conduct searches from any Web browser.

Still yet another object of the invention is to permit health care providers to conduct searches from any Java-enabled Web browser.

Another object of the invention is to make possible the interoperability of widely-used desktop applications within the deeply fragmented healthcare industry.

Another object of the invention is to provide a way that every word in a computer-based patient record (or records index) database is indexed with a gateway to the World Wide Web.

A further object of the invention is to provide a means by which these indexed words are made available to searchers through a system designed to assure both the privacy of these records and the security of the legacy systems on which the original documents are held.

Yet another object of the invention is to provide easy and rapid migration of new computer-based patient record systems and applications in the future as set forth in U.S. Pat. No. 5,301,105.

Still yet another object of the invention is to readily search a master index of patient records through the Internet or intranet.

Another object of the invention is to automate the approvals process required in order to retrieve relevant items identified as a consequence of a search of patient records and/or indexes thereof.

Another object of the invention is to improve the quality of patient care, reduce the cost of healthcare, and eliminate duplication of efforts.

A further object of the invention is to deploy data warehouse/decision support system (DW/DSS) technologies to a large numbers of users across organizational boundaries while relying upon conventional client/server technology.

Yet another object of the invention is to optimize the use of the Internet and World Wide Web as a distribution channel for personal medical records without compromising the vital healthcare and professional service industry considerations of confidentiality, privacy and economics.

Still yet another object of the invention is to provide for authentication of the identity of the requesting party in any database search.

Another object of the invention is to provide for authentication of the identity of the party about whom the records pertain in any database search, and to provide such person with an express opportunity to either approve or decline whether such records may be transferred on a case-by-case basis as database search requests are received.

Another object of the invention is to prevent tampering and message forgery of the means for authenticating the identity of the persons requesting a database search, the person about whom the records pertain and any other parties whose express permission is required in order that such records may be transferred.

A further object of the invention is to assure that every step in the approvals process is appropriately completed.

Yet another object of the invention is to provide a means by which the person requesting information can determine the approximate time period required to retrieve and deliver the information once all approvals are complete, the available type(s) of media on which the document can be delivered and the cost (if any) for this information to be forwarded to the requesting party.

Still yet another object of the invention is to provide a quick and intuitive means for the searcher to specify which records they would like to retrieve, indicate a priority level for this to occur, select the preferred means for transmittal of the documents and confirm the payment arrangements with the party holding such records.

Another object of the invention is to provide searchers with a means to create a "standing order" that will automatically prompt an attempt to retrieve certain types of materials and information under pre-specified circumstances.

Another object of the invention is to make possible contacts with persons who do not have an email account by provision for automatic generation of a fax, letter or phone call to communicate approvals requests to such persons.

A further object of the invention is to provide for the administrator of the database where the records are held to specify in advance the condition or conditions which must be met in order for the release of this information to occur from such database.

Yet another object of the invention is to enable this approvals process to occur without requiring any case-by-case action by the database administrator, and thereby to avoid any waste of resources on those requests for which a party does not grant specific authority for a copy of the records to be shared with the requesting party.

Still yet another object of the invention is to provide the requesting party a means by which to designate certain requests for priority action and thereby expedite these requests.

Another object of the invention is to permit complete control over all documents in the hands of the data administrator, while simultaneously undertaking on such administrator's behalf through the system all of the time-consuming paper-intensive and often thankless tasks involved in securing proper proof and documentation for releasing inherently sensitive medical records.

Another object of the invention is to provide a means to accommodate records that are stored off-line and that require magnetic tapes to be mounted and/or copies to be made of documents preserved in a non-digital form, such as in paper records, x-rays, photographs, and on micro-fiche or floppy disk.

A further object of the invention is to create a comprehensive security log which can act as proof that all authorizations for release and/or transfer of the records are complete.

Yet another object of the invention is to provide complete security of data and data bases together with an off-site audit trail.

Still yet another object of the invention is to permit data administrators a means by which to keep their system that is connected to the Internet or an intranet physically disconnected from the legacy system on which sensitive records are held except during the batch process of uploading pre-designated and fully-approved requests for such documents.

Another object of the invention is to provide secure protection of the legacy system and thereby to make it virtually impossible for a person to gain unauthorized access to that computer system or any of the records contained on it.

Another object of the invention is to provide a secure online cache for temporary storage of requested information from the legacy system.

A further object of the invention is to provide a means for informing the requesting party when any documents previously requested have been submitted to the temporary cache and are, thus, available for their use.

Yet another object of the invention is to provide tracking information concerning all transmitted materials, which information can be used to locate these documents in the event they are not timely received.

Still yet another object of the invention is to provide a means to dramatically reduce response times required for a searcher to get copies of highly confidential and private data or records, thereby significantly lowering overhead costs, while maintaining total document control and security.

Another object of the invention is to allow for presentation of display advertising as a means by which to help defray costs associated with creating and maintaining the system.

Another object of the invention is to provide for the integration of electronic commerce features that will enable hospitals, testing labs, physicians, and the like, to charge for the transfer of a patient history, comprehensive medical records, lab reports, test results, prescription drug records, administrative and payment records as a further means by which to help defray costs associated with creating and maintaining the system.

A further object of the invention is to provide an indication of the status of a searcher's request, and of the transfer of requested documents pursuant thereto.

Yet another object of the invention is to provide an incentive to physicians to upgrade their office computing systems.

Still yet another object of the invention is to shift the administration of patient records from being a cost center to a profit center.

Another object of the invention is to provide an incentive for organizations to make their information as relevant as possible to others in the healthcare industry.

Another object of the invention is to provide a means by which the traditional information flow (from a centralized database, hospital or lab TO an individual physician) can also function in reverse, depending on the types of information requested, and to thereby permit patient records held by independent doctors' offices and clinics to be as accessible as data held in a central data base warehouse, including any hospital or testing laboratory.

A further object of the invention is to provide a means for secondary researchers to review as broad a database as possible from searching of patient records in order to support their research efforts, treatment efficacy studies, expert systems, artificial intelligence programs and other efforts to improve future decision-making and payment processes as set forth in U.S. Pat. No. 5,301,105.

Yet another object of the invention is to permit physicians to share patient records with authorized third-parties without incurring a significant increase in time or administrative overhead costs.

Still yet another object of the invention is to permit physicians to share patient records with confidence that litigation will not ensue concerning their having breached patient confidentiality, and that will assure the presence of full evidentiary documentation of the propriety of such action in the event there is a subsequent question concerning their action.

Another object of the invention is to speed up and reduce the cost necessary to conduct the adjudication and utilization review functions set forth in U.S. Pat. No. 5,301,105.

Another object of the invention is to expedite and reduce the cost of medical review and payment evaluation procedures desired for healthcare reform in order to lower overall costs.

A further object of the invention is to provide a means for comprehensive protection for the confidentiality and integrity of computer-based patient records.

Yet another object of the invention is to provide a means for comprehensive protection for the confidentiality and integrity of the data networks that carry medical records and information.

Still yet another object of the invention is to provide a more secure, more error-free and tamper-resistant system for accessing medical records.

Another object of the invention is to allow patients the opportunity to give specific informed consent every time that any information about them is desired by third parties—a level of control and protection which according to a recent TIME/CNN poll, 87% of all Americans indicate they desire, but which extensive contemporaneous testimony by industry leaders indicates is not available, unlikely and/or impossible given all known and foreseen technology.

Another object of the invention is to reduce the risk of exposure to litigation alleging breaches of patient confidentiality by persons and institutions holding and/or transferring medical records.

A further object of the invention is to allow different types of databases to be accessed and to thereby permit numerous organizations and software developers to work in parallel to write enhancements, to customize individual installations and to provide additional functionality without reducing the ubiquity of the overall system.

All of the foregoing features are integrated and include interactive participation with healthcare providers and trustees.

The foregoing and other objects and features of the invention will be apparent from the following detailed description, by way of a description of a preferred embodiment, with reference to the drawings.

Other objects and advantages of the present invention will become apparent from the following descriptions, taken in connection with the accompanying drawings, wherein, by way of illustration and example, an embodiment of the present invention is disclosed.

The drawings constitute a part of this specification and include exemplary embodiments to the invention, which may be embodied in various forms.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

While the instant invention is applicable broadly to systems and methods of searching data bases requiring prior approval for confidential access, it will be described with respect to medical records data bases accessible over the Internet where access requires approval by one or more third parties, such as a patient. It will be evident that a local area network (LAN), intranet or wide area network (WAN) can also be utilized.

Figure 1:
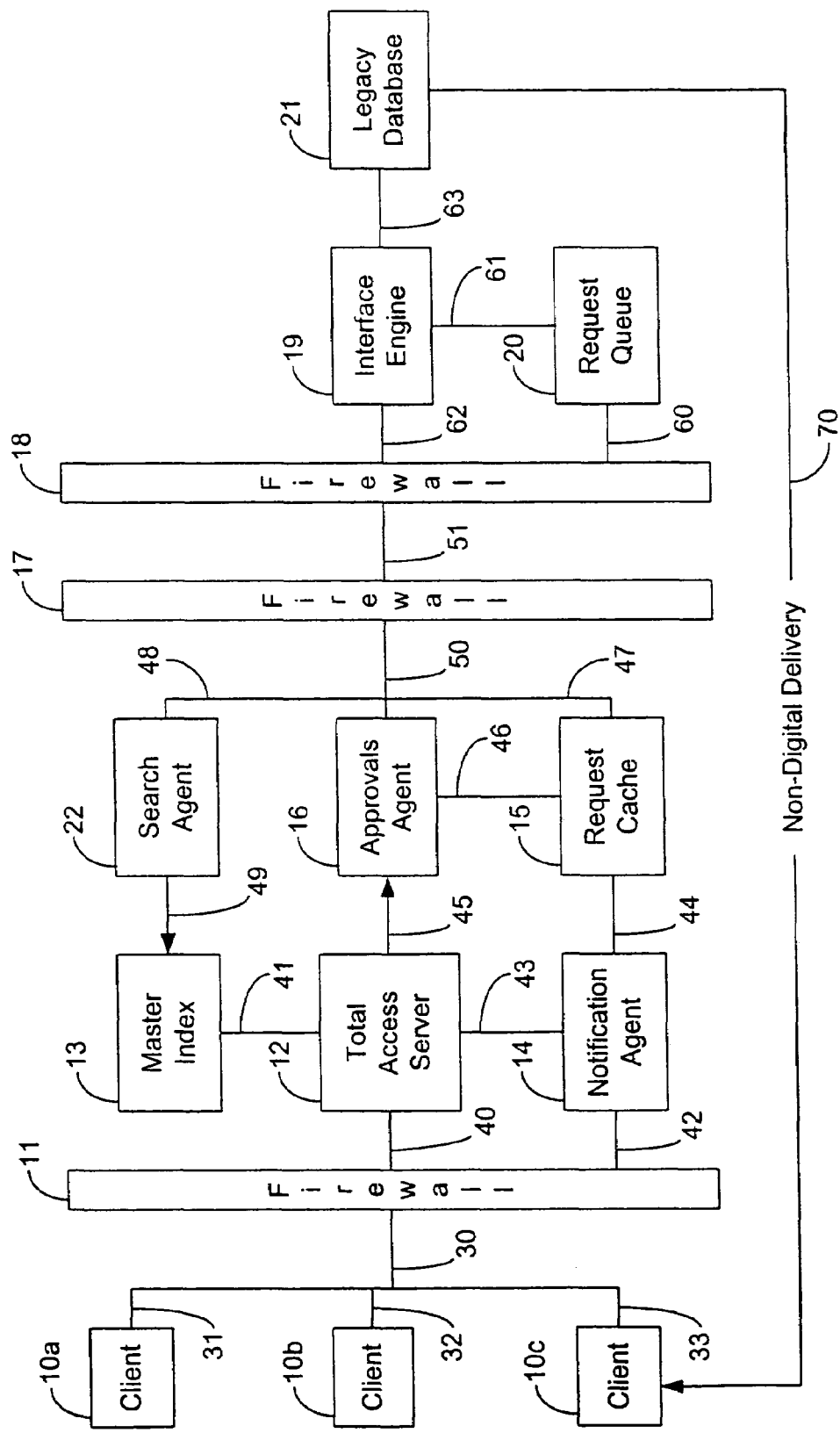
FIG. 1 is a block diagram depicting principal functions of the instant invention as applied to searching medical records data bases.
Figure 2:
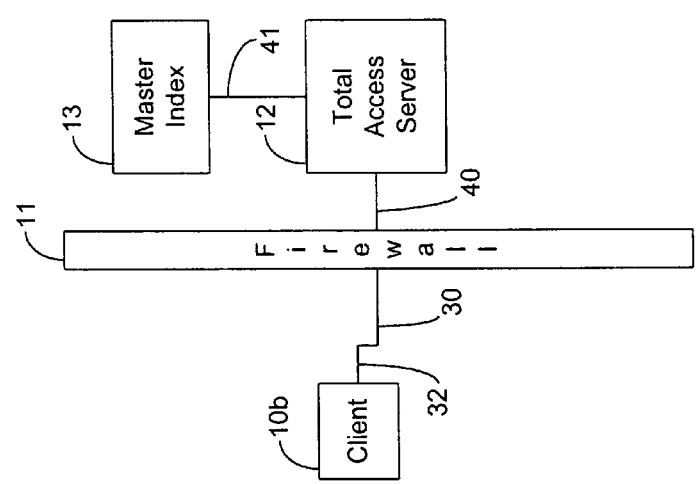
FIG. 2 is a block diagram illustrating process flow of the search of the index of information of interest portion of the system and method.
Figure 3:
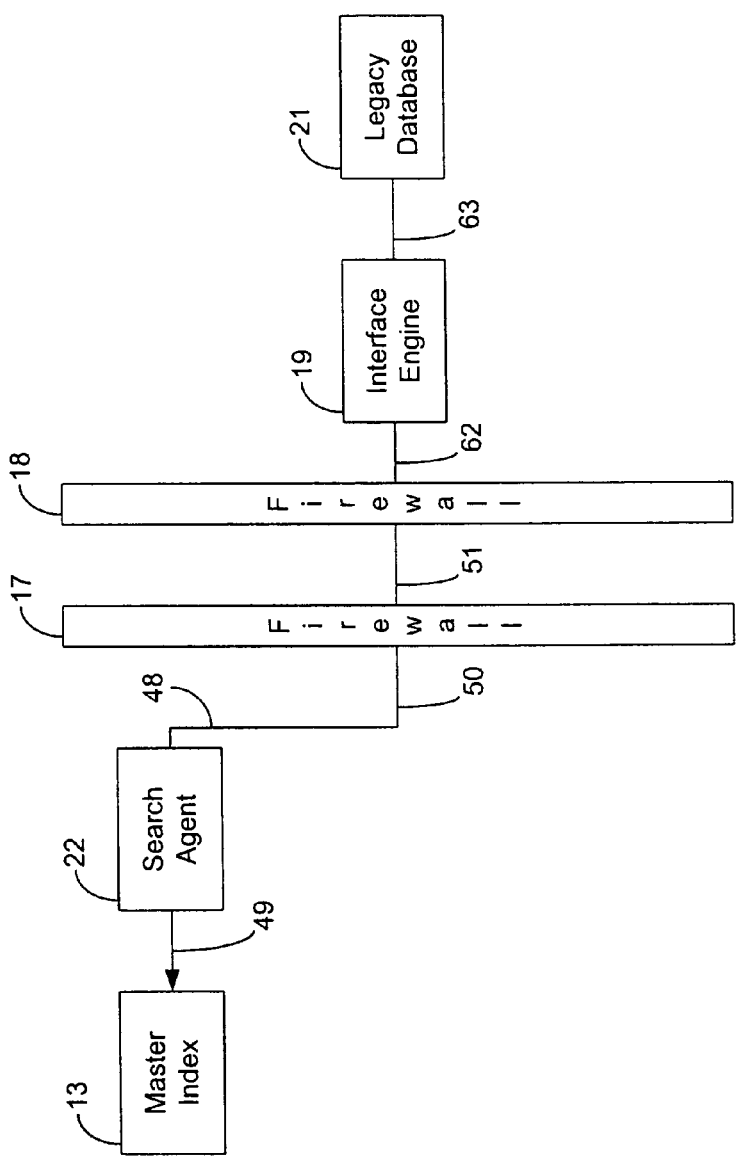
FIG. 3 is a block diagram illustrating process flow of the periodic updating of the searchable index portion of the system and method.

Referring to the drawings, FIG. 1 depicts the principal components of a preferred system in accordance with the principles of the invention. Shown as 10a–10c are clients; i.e., healthcare information users requiring access to medical records and patients for whom such records are held. Such healthcare information users can be hospitals, doctors, nursing services, nursing homes, insurance companies, patients, druggists, employers, and the like. For ease of illustration the invention will be further described with the healthcare information user being a doctor.

Before describing the system and method in detail and referring to the drawings, it will be evident that the client, i.e., the doctor, will need to have an adequate conventional computer terminal and printer and that the terminal be connected as by telephone 31, 32, or 33, or satellite or other means to the Web by means of any conventional Internet service provider. Links 30, 40 to 51 inclusive, and 60 to 63 inclusive are likewise conventional communication paths such as telephone lines, internal connectivity, or the like, all operating through the Internet through Internet firewall gateways 11, 17, and 18. All of these are conventional presently existing techniques for accessing and gathering information from the Internet. It is also possible, of course, to utilize an intranet, LAN or WAN, in lieu of the Internet.

By operating through a conventional Internet service provider, there will also be available to the client an electronic mail function linked to the processing system, i.e., the doctor's computer and printer. While the present invention does provide for Non-Digital delivery 70 from a Legacy Data Base 21, it will be evident that for ease and speed of transmission, it is preferable to utilize electronic mail.

In short, the instant system and method utilize existing computer hardware and existing communication links, such as the Internet and intranet, in order to access data bases without compromising the vital considerations of privacy of patient information and rigorous control of access, as well as retaining records of the access requester.

Moreover, as used herein, the terms, "server", "cache", "interface engine", "queue", and "agent" have the standard meanings used by those skilled in this art. The term "Legacy Data Base" means any existing data base such as a doctor's records or medical records of a hospital, nursing home, and the like. "Master Index" means an index of information in the system. Lastly, "Firewall" refers to the usual known security layer(s) provided in computerized systems to permit access to certain files only to those having the necessary "password(s)". The Internet, for example, gives users their own private password.

To initiate a search, the requesting physician, 10b, will simply enter through his or her computer the search criteria into the relevant query fields and press the submit button. Although this search can be initiated from any Java-capable Web browser, originating a search request will require authenticating the identity of the requesting party, as is presently conventional with Web users.

When the request is made from the physician's own machine, this can occur through a digital certificate, such as VeriSign's Class 2 Digital ID. If the requesting physician is using another machine as a guest, authentication can occur through a smart card such as offered by a number of firms to provide irrefutable evidence of the owner's identity. All traffic can be encrypted to prevent tampering and message forgery. Firewall 11 prevents any unauthorized entry.

Generally, the query will be divided into two parts. The first will identify the patient, and may include their name, Social Security number and any other identifier used from time to time. The second part will consist of a word, or a series of words, that will narrow the search results to the topic of interest.

The search interface will also permit the optional use of boolean operators and a number of other search parameters including data type, document type, start and end date for the records, ordering physician's name and locations where work was previously conducted, in order to more accurately specify what he or she is looking for.

After entry is approved and the order submitted, the search engine, Server 12, will produce a prioritized index from Master Index 13 of all documents meeting the specified criteria, together with a hypertext link or similar connection to an order form for securing a copy. The search results will report the approximate number of documents found that match the search criteria; the title and type of each such document; and the date it was created, name of the ordering physician and location (or locations) where these records are held.

The instant system and method have conventional associated software with suitable graphical user interface and readily-understandable icons for key functions. The physician can simply click on the icon associated with any item on the list and this will bring up its first 1–3 lines of text or other description of the document and an order form indicating all of the approvals required before the holder will release it. This form will also specify the approximate time period required to retrieve and deliver the information once all approvals are complete, the available type(s) of media on which the document can be delivered and the cost (if any) for this information to be forwarded to the requesting party.

Through a series of programmed commands, such as mouse clicks on a results form, the physician will specify which records he or she would like to retrieve, indicate a priority level for this to occur, select the preferred means for transmittal of the documents, and confirm the payment arrangements. Alternatively, the physician can create a "standing order" that will always attempt to retrieve certain types of materials, such as "Give me anything you have in the way of blood work for all known identifiers used for this patient over the last 3 years. Use the fastest transmission means available. Payment for all related charges guaranteed."

Figure 4:
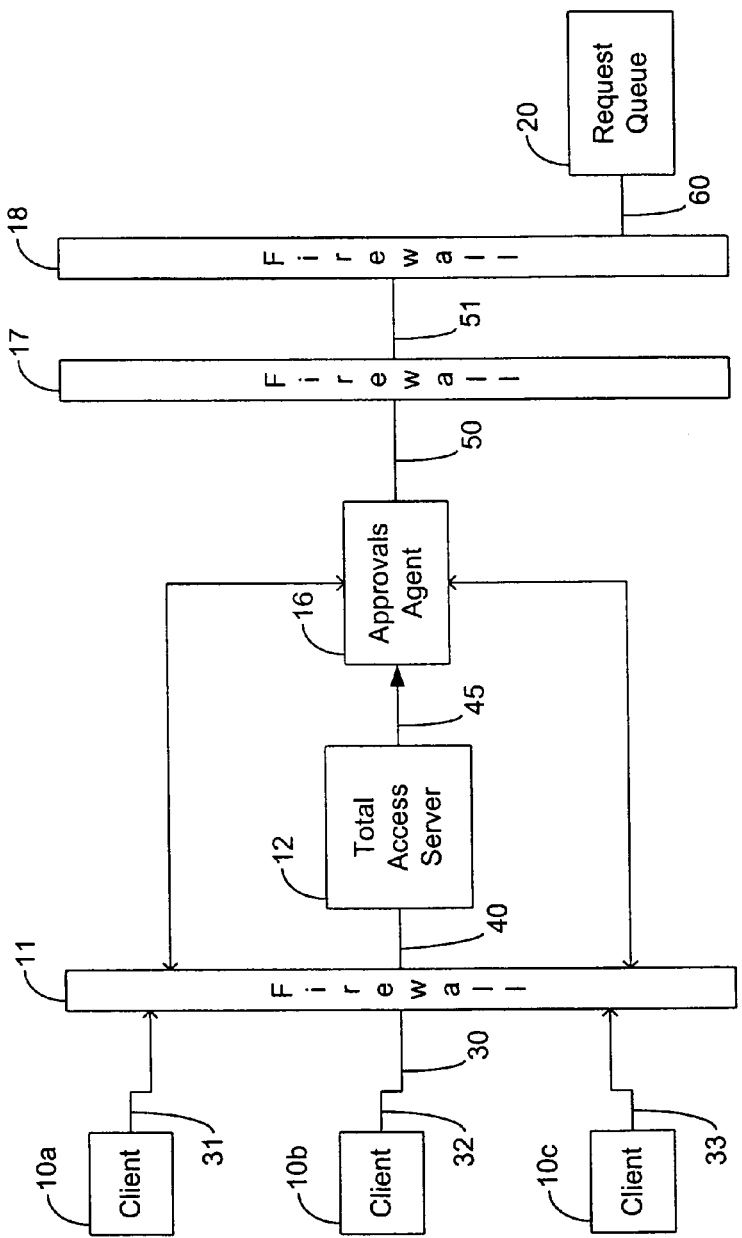
FIG. 4 is a block diagram illustrating process flow of the request and approval portion of the system and method.

As shown in FIGS. 1 and 4, both the initial order process and standing order database request will initialize a workflow agent, represented by Approvals Agent 16, to seek the relevant approvals indicated by the data administrator or the Legacy Base 21, where the records are held. Although E-mail is the preferred means to communicate this request for approval to release this or these records, Approvals Agent 16 can also automatically generate a fax request, telephone call or machine-generated conventional letter to any persons who do not have an E-mail address.

Data items may be categorized with attributes which identify levels of sensitivity, accessibility, release approvals required and other related considerations relevant to access, encryption, authorized mode of transfer, and the like. Thus, when a request for release is received, the relevant attributes provide a ready way to automatically obtain important customized information tailored to each individual data item.

By way of illustration, a patient may give prior approval and it be on record in the system as a data item that as to any future request by any doctor or medical institution, there is the automatic pre-authorization by such patient for the release of his medical data to such doctor or medical institution.

The second stage search service begins when the doctor submits a completed order form. Approvals Agent 16 acts as a message-passing server, responding to the orders it receives and the conditions prescribed by the data administrator of any Legacy Data Base 21 for release of this information, and in turn, contacts other resources over the network or via fax to secure these approvals. In an ideal circumstance, such persons will be other clients 10a and 10c, but could be persons outside the user's with known connections to the Internet.

For standard turn-around, this automated process of securing all related approvals is undertaken before the data administrator is informed that a request has been made for these records. This avoids any waste of resources on those requests for which one or more party does not grant authority for a copy of the records to be shared. In expedited requests, the data administrator will be informed with respect to any materials that have a longer lead time so that these can be placed into the queue for immediate processing once the required approvals are secured.

The parties who's approval is required by the administrator of the Legacy Data Base 21 where the records are held, will receive an automatically generated message from the Approvals Agent 16, indicating that a request has been made for the records selected by the requesting client 10b. This message will specify the name of the requesting party, the nature of his or her interest, the title and location of the document requested, and a summary description of the information being sought, as well as the date on which it was created, and such other information deemed appropriate for time-to-time. The notice will provide an icon for easy selection by the recipient to indicate his or her consent, or denial, of such provision together with means for authenticating his or her identify, all expressly applied by the data administrator.

In the event the party is not one of clients 10a or 10c, but rather is an off-line user, the approval agent will automatically generate a request by a facsimile or mail to the last known address of the party. Alternatively, if a standing provision has been given by the party for release of their records in the specific circumstances fulfilled by the requester, then such approvals will be granted automatically. In the event of faxed or mailed approval requests, the recipient will be asked to contact the requesting client, 10b, or the administrator for the Legacy Data Base 21 to indicate his or her approval and to provide evidence of such consent, together with proof of his or her identity.

This implementation system and method leave control over all documents in the hands of the data administrator, while simultaneously delegating to the instant system all of the time-consuming, paper-intensive and often thankless tasks involved in securing proper proof and documentation for releasing inherently sensitive medical records.

The instant system and method take into account the likelihood that many of the requested records may be stored off-line, requiring magnetic tapes to be mounted and/or copies to be made of documents preserved in a non-digital form, such as in paper records, x-rays, photographs, and on micro-fiche or floppy disk.

When Approvals Agent 16 receives all of the required authorizations for release of the records request, it will automatically generate a message to the data administrator where these records are held notifying him of this fact and asking that he retrieve and transmit the documents to the requesting physician. This notification will also include a copy of the security log showing proof that all authorizations are complete; specify the requested mode of transmittal (e.g., mail, fax, overnight delivery or network transmission) and verify that all related charges are paid If the Approvals Agent "times out" before all approvals are in place, it will automatically generate a message to the requesting party, client 10b, indicating the name of the person or persons whose approval or approvals have not been received so that the requesting client may attempt to contact that person or persons directly or, alternatively, to terminate the document retrieval request.

According to a 1996 survey of 1,320 chief information officers (CIO's) and other senior information executives conducted by Ernst & Young/InformationWeek, "nearly three-quarters (71 percent) of the executives surveyed expressed a lack of confidence in the security of their computer networks", and listed an unsecured Internet connection as one of the major areas of vulnerability. The instant system provides complete security and an off-site audit trail.

The present invention provides three layers of security for data in any Legacy Database 21, which horizontal rectangle is meant to include records held in both an on-line digital form, including in a data mart, warehouse or the like, as well as off-line in digital form, and off-line in a non-digital form, such as on diskettes, magnetic tapes, paper or micro fiche, or the like. For purposes of this description, the preferred embodiment will be a digital record or "computer-based patient record", often referred to in the field as a CPR. First, the message asking release of the records will only originate from the system bot (meaning computerized robots), authenticated by its own unique digital signature, as opposed to an unknown network user. Second, the request will be made to the data administrator, who's computer where this Request Cache 20 is maintained can be kept physically disconnected from the Legacy Database 21 except during the batch process of uploading pre-designated and fully-approved documents. And finally, this process will involve manual entry—albeit very easy as through clicking on designated icons—by the data administrator, who acts as a last filter in the case of observing any unusual activity in the Request Queue 20.

The present system and method provides a graphical user interface (GUI) which will prompt the administrator to enter the tracking number for any records that are transmitted other than by the Internet, including by courier, mail, or facsimile; and will note the actual date of transmittal via such other modes. Those documents that are held as on-line computer-based patient records will be replicated and transmitted to the Request Cache 15 over the network via connections 47, 50, 51, 62, and 63.

Figure 5:
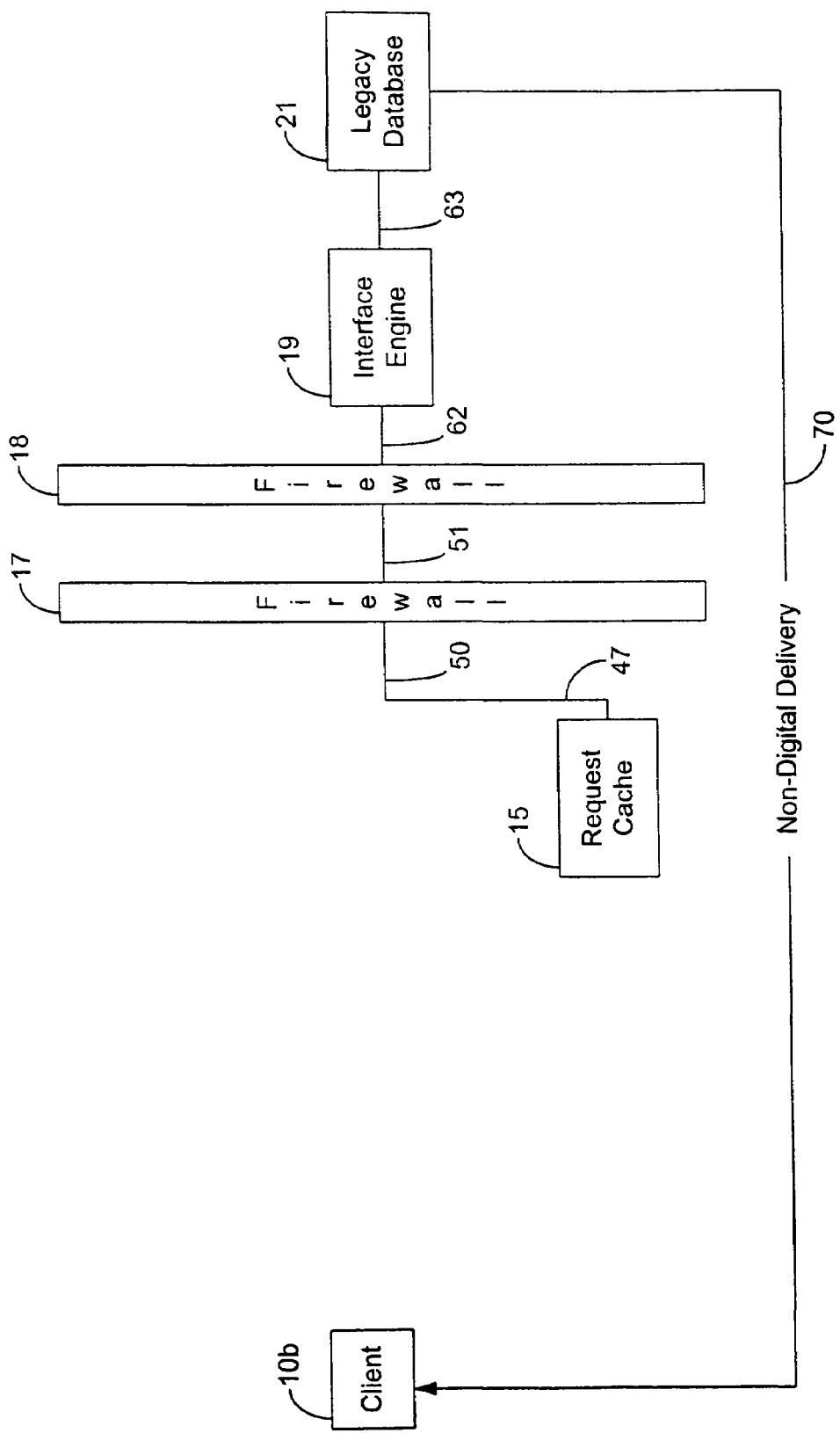
FIG. 5 is a block diagram illustrating process flow of the data requested to an on-line cache memory portion of the system and method.
Figure 6:
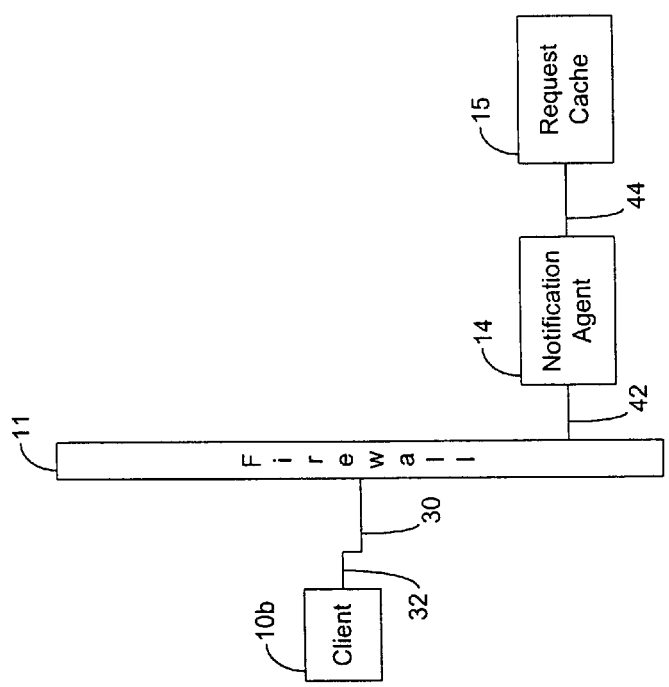
FIG. 6 is a block diagram illustrating process flow of the notification of availability for retrieval, or tracking of information in accordance with the instant invention, and for the upload of such information when in a digital form.

As noted, once all required approvals have been secured for the data, the records that are in digital form are uploaded to a secure Request Cache 15, linked to Server 12, rather than directly to the requesting physician 10n. Receipt of the upload or of a message confirming that the document(s) have been sent outside the system by non-digital delivery indicated by line 70 in FIG. 5 triggers Notification Agent 14 to inform the doctor 10b.

This system and method, similar to the well known "store and forward" technique used in many data bases, results in several advantages. Since there is never a direct connection established between Legacy Database 21 and doctor 10*b*, the design adds one more layer of security. This same architecture supports near-real-time and real-time transmissions if such nature is merited by the priority established by the requesting physician, the approvals conditions stipulated by the data base administrator, and the standing order provisions established by the patients affected.

In addition, the Request Cache 15 eliminates the requirement for the doctor 10*b* to be on line at the time the upload takes place from the Legacy Database 21. A message is sent by Notification Agent 14 that informs doctor 10*b* that the requested document(s) are available and provides a hypertext or functionally comparable link for retrieval of this information from Request Cache 15. In instances when any document is not in a digital form and was sent by mail, facsimile or courier, Notification Agent 14 will confirm the date and time of transmittal, and provide tracking information that can be used to locate these documents in the event they are not timely received.

Upon being notified that the document(s) containing the requested details in Request Cache 15, doctor 10*b* will be able to log onto the Internet from any browser, go to the instant system Web site, authenticate his or her identity, and then selectively retrieve and review these files. Following review, the documents can either be discarded, copied to a local drive or printed. Alternatively, doctor 10*b* may request that the information be retained for a specified period of time on his or her behalf in a secure data warehouse, which can be a partitioned part of the Request Cache 15, or an interconnecting computer used for such purpose (not shown).

The foregoing system and method assures that all parties' interests are protected at all times. The method will dramatically reduce response times, significantly lower overhead costs and maintain total document control and security information since these important steps will all be carried out efficiently and transparently by the system.

Periodically, search agent 22 will have provisions from the data administrator to search the Legacy Database 21 and update the Master Index 13 with every word in every computer-based patient record (or records index) database with a gateway to the World Wide Web. In the event such records are in a computer language other than established by standards bodies for Internet transmission, the system and method incorporates an interface engine 19 to translate the records and thereby make them available using the Internet. This interface engine 19 can also be used to indicate which of the records are indexable and which are retrievable on an item-by-item basis, all as specified by the data base administrator and/or by instruction of the patient.

As will be evident to persons skilled in the art, these attributes will make all of the records available to searchers through the system described and simultaneously assure both the privacy of these records and the security of the legacy systems on which the original documents are held. The invention represents improvements over existing records data bases in five key areas: records indexing, access control, automated approvals processing, transactional billing and secure document caching.

It will be evident from the foregoing description that rather than conceiving a new database server, data mart, database warehouse or interface engine to compete with existing systems, there will be utilized such systems as are already on the market or currently under development by literally hundreds of firms including Microsoft, IBM, Hewlett-Packard, Sybase and SMS. The instant invention embraces and integrates over the Internet all of the major database systems built for the healthcare industry and patient records packages running on popular desktop, server and legacy operating systems and organizations with intranets. This concurrently lays the groundwork for easy migration of new computer-based patient record systems and applications in the future by creating a master index of patient records that is easily searched through the Internet.

This results in greater extensibility and a number of capabilities not achieved with other technologies, or other known combinations of technologies mentioned above.

The AltaVista Public Search Service developed by Digital Equipment Company and other Internet search engines illustrate that while the Internet remains essentially unstructured, it is possible—with enough software sophistication and computing power—to catalogue the connected realm. To index every word on every page of every available Web site, and to make these available to searchers without adding arbitrary structure or categorization. In effect, as Digital states, "to bring order and meaning to an otherwise unwieldy behemoth."

While most of medical records existing today are not even "on the Internet", more and more is being put into a form that can be put on the Internet. This creates the capability for a doctor to quickly and intuitively search for his or her patient's prior medical records, and automates the approvals process required in order to retrieve relevant items indicated within this index.

Moreover, though there are today only a few healthcare databases with a TCP/IP or HTTP compliant interface to index, this provides an opportunity to grow with the migration of technology to the language of the Internet and the transactional payment through electronic commerce means provides an economic incentive for this to occur. By the same token, as Ernst & Young concluded in their recent study entitled *The Role of the Internet in Health Care*: "The Internet is becoming a pervasive force in today's global economy and healthcare organizations need to be strategically positioned to participate." The relevance of the instant invention is to improve the quality of care, reduce the cost of healthcare and eliminate duplication of efforts as increasing numbers of medical databases are connected to this new distribution channel.

Michael Saylor, President of MicroStrategy Inc., selected by Database Programming & Design Magazine as one of the twelve most influential companies in the database industry, predicts that the economic potential of employing the World Wide Web to publish information held in data warehouses to users outside of the corporations which own these legacy systems could represent a hundred-billion dollar market.

In its preferred form, the instant invention is designed with three primary "stakeholders" in mind: the physician, the IS/IT administrator and the patient. Unlike any other medical search engines, the instant invention takes full advantage of the Internet to access institutional databases while taking into consideration the competing requirements of rapid access to patient records and medical information, security, privacy and economics.

The value of the information in these existing records and data repositories is extraordinary. Notwithstanding, the healthcare industry has so far extracted only a small fraction of the value from these archives. This is principally due to the extraordinary difficulty of deploying data warehouse/ decision support system (DW/DSS) technologies to large numbers of users across organizational boundaries while relying upon conventional client/server technology. The instant invention overcomes this difficulty through the specially designed indexing and search system that will optimize use of the Web as a distribution channel without compromising the vital industry considerations, such as privacy, which are unique to healthcare where it is well known that patients and patient advocacy groups are becoming increasingly aware of the risk of privacy breaches in the future as technologies improve.

Typically on the Internet, a larger computer functions as a server and a smaller computer (for example, a work station) as a client. Something similar is also true in healthcare where the legacy database systems maintained by hospitals and large testing laboratories are typically the data providers; and the individual physician's offices are most often the data consumers.

The system of the present invention takes full advantage of the Internet's distribution capabilities and permits this information flow to also function in reverse, depending on the types of information requested. Although not shown in the drawings, another client could be the repository of the data, in fact, acting within the system as Legacy Data Base 21. This capability is particularly vital in the healthcare industry since much of the patient record is distributed between independent doctors' offices and clinics rather than held in a central data warehouse, as in other industries.

As increasing numbers of physician offices computerize patient records or build computerized indexes of their non-digital records, the instant invention will make this information available to other medical professionals. The system's automated processes, on line cache and electronic commerce features will permit physicians to offer this service without a significant increase in time or administrative overhead; and will provide an economic return to the physician when his or her office provides patient records to other medical professionals.

As discussed above, the instant system's fine-grained controls limit access to documents, directories and database sites. Over the short term, these controls can be designed to restrict access for individual patient records. As inference engines, artificial intelligence algorithms and other expert systems technologies become more refined and better standards for computer-based patient records are adopted for the industry, the system's architecture also lends itself to filtering content and automating the research process involved in making abstractions over wide databases of individual patient records. This capability serves as an important step toward incorporating the adjudication and utilization review functions set forth in U.S. Pat. No. 5,301,105 and the medical review and payment evaluation procedures suggested in a number of industry white papers and well-regarded articles concerning healthcare reform.

The healthcare industry has access to very large machines and broad communications bandwidth. In this sense, another advantage of the instant invention is that it provides a means to broaden the network of physicians who can use information contained in existing records databases, as well as adding new database sources in a way that is less costly and significantly faster way to implement than using traditional methods. Over the longer term, as use of the Internet and computer-based patient records increase, the logic of the instant system and method becomes even more compelling. The use of open-standards allows for more rapid integration of numerous third-party technologies as well as for the creation of custom in-house solutions.

Encryption of all communications using secure sockets technologies such as SSL 3.0, and more robust Internet security standards that will supersede it in the future, will prevent tampering, eavesdropping and message forgery. By the same token, computer networks are only as strong as their weakest link, which is often the gateway. Employing the instant system "as" this gateway enhances this network security, while at the same time facilitating faster access to patient records and vital medical information for a much broader audience through the Internet.

The present invention makes it fast, economical, convenient and extremely easy for physicians and other medical professionals to make more extensive use of these records in their daily practice of medicine. The system simultaneously makes it practical for data administrators both to manage and economically benefit from this increased demand for patient records and medical documents they control.

In 1995, Senator Robert Bennett (R-Utah) introduced the so-called Medical Confidentiality Act of 1995. Although the legislation remains mired in debate, one thing has become clear from remarks made by both the staunch advocates for the legislation as well as its numerous dissenting voices, most of which, like the ACLU, and various other citizen advocates, feel that its protections are inadequate. The fact is that comprehensive protection must be devised that will guarantee the confidentiality and integrity of computer-based patient records as well as the data networks to carry such information.

One of the primary advantages of the instant invention is that it will use today's advanced technologies in order to create a more secure, more error-free and tamper-resistant system for accessing medical records than exists in a non-computerized environment.

According to a TIME/CNN poll, most Americans (87% of respondents) believe patients should be asked for permission every time any information about them is used. The present invention makes it possible to achieve this ideal for those persons who demand it, and to pass along the attendant costs associated with this higher standard of administrative care to these persons. Hence, rather than attempt to impose one solution that will be good for everyone, this invention is designed to permit each stakeholder to set their own conditions for the transfer of this highly personal information. This system operates strictly as an honest broker. It negotiates the conditions and then carries out the transfer of information only AFTER these requirements have been fulfilled. And when information does move, the system keeps complete and accurate logs that document exactly what happened, when, why and with who's express consent so that there is strict accountability.

The instant system's central premise is that the patient has a fundamental right to the confidentiality of their records and should control that right through specific, informed consent. It reinforces the widely held conception of privacy in general as well as of the sanctity of the doctor or other trustee relationship by granting the doctor the right, subject to the patient's express permission, to initiate a search request. At the same time, it gives the repositories where these records are held the right to stipulate the specific terms and conditions that must be fulfilled before they will release documents entrusted to their care, thereby substantially reducing the risk of litigation alleging breaches of patient confidentiality. And it carries out all of these legitimate interests of all parties in a way that is fast, simple to use and easy to audit.

Accordingly, like several existing Internet-based services, the instant invention consists of the query interface described in the preceding sections and a separate, fully automated Search Agent 22. This automated software robot will collect data to be stored and queried in the Master Index 13 from any records database (or database index) connected to the Web which is either TCP/IP or HTTP compliant, or whose native language has been "translated" into being compliant through one of several commercial interface engines and system capabilities the present system incorporates in the Search Agent itself. Master Index 13 automatically produces links to every word in every record brought back by the Search Agent 22, eliminates duplicates and uses a ranking system so when doctor 10c performs a query, the most relevant and useful results are more likely to be reported at the top of the list.

While the invention has been described in connection with a preferred embodiment, it is not intended to limit the scope of the invention to the particular form set forth, but on the contrary, it is intended to cover such alternatives, modifications, and equivalents as may be included within the spirit and scope of the inventions as discussed herein.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A medical data base supervisory control system comprising:
    (a) at least one data base including medical data individually relating to each of a plurality of patients,
    (b) means including interconnected computers for requesting and accessing said medical data,
    (c) means for identifying medical data for each of said patients with conditions required for accessing said medical data, and
    (d) data processing means responsive to a request for patient medical data for comparing said request with said conditions required for access to said data and, when said request fails to comply with said conditions, for denying access to said data.

2. A system of claim 1 further including means for authenticating the identity of the requesting party.

3. The system of claim 2 further including means to prevent access to information concerning medical records by any party without the prior authorization of the patient about whom such records pertain.

4. The system of claim 1 further including means for tentatively identifying records fulfilling criteria specified in said request for medical data.

5. The system of claim 4 further including means for authenticating identity of said patients.

6. The system of claim 1 wherein said means for requesting said medical data includes means for indicating what part of said records is desired.

7. The system of claim 1 wherein said means for requesting access to said medical records includes means for indicating the reason said records are being requested.

8. The system of claim 1 further including means for identifying records fulfilling said request with data symbolic of patient identity.

9. The system of claim 8 wherein said means for identifying records fulfilling said request further include data symbolic of medical symptoms or reason for patient visit.

10. The system of claim 8 wherein said means for identifying records fulfilling said request further include data symbolic of types of diagnostic tests performed.

11. The system of claim 10 wherein said means for identifying records fulfilling said request further include data symbolic of the attributes, levels or findings indicated within said diagnostic tests.

12. The system of claim 8 wherein said means for identifying records fulfilling said request further include data symbolic of modes of treatment or medical services rendered.

13. The system of claim 8 wherein said means used for identifying records fulfilling said request further include data symbolic of any ancillary services rendered.

14. The system of claim 8 wherein said means used for identifying records fulfilling said request further include data symbolic of attending physician identity.

15. The system of claim 8 wherein said means for identifying records fulfilling such request further include data symbolic of date of care.

16. The system of claim 1 wherein said means for requesting and accessing said medical data includes means for indicating a "standing order" that will automatically initiate an attempt to retrieve certain predetermined types of medical data under specific pre-specified circumstances.

17. The system of claim 1 wherein said conditions required for accessing said medical data includes an indication of the names of each of the parties who's permission must be obtained prior to the release of the medical data.

18. The system of claim 17 wherein said conditions required for accessing said medical data further includes an indication of the charge that will be assessed by the holder of such medical data for the part, or in the form, specified by the requesting party.

19. The system of claim 17 wherein said conditions for accessing said medical data includes means indicating the time following the receipt of all approvals that will be required for the delivery of such medical data to the requesting party.

20. The system of claim 1 wherein said at least one data base includes a firewall limiting access to searching such data base solely to those parties who are authorized to do so.

21. The system of claim 1 wherein said means for identifying medical data fulfilling criteria specified in a request include means for producing an indicia of the degree to which patient data match said criteria specified in said request.

22. The system of claim 1 including means for a patient to grant permission for the release of his/her medical data.

23. The system of claim 22 wherein said at least one data base includes billing means having access to said medical data.

24. The system of claim 22 wherein said means for a patient to grant permission includes data symbolic of the identity of said patient and data symbolic of the preferred means for contacting said patient to request access to and release of said patient's medical data.

25. The system of claim 23 wherein said means for a patient to grant permission includes data symbolic of rules to be followed in the event time elapses before such permission is granted in the case of predetermined types of requests for said medical data.

26. The system of claim 1 further including means for identifying the party requesting access to said medical data.

27. The system of claim 26 further including means for authenticating the identity of each party having right of approval for release of said medical data.

28. The system of claim 27 further including means for producing an indicia that all required approvals for the release of said medical data have been secured.

29. The system of claim 28 further including means for producing an indicia of the required approvals for the release of said medical data that have not been secured or that have been specifically declined.

30. The system of claim 20 further including data index means and on-line memory cache means for physically disconnecting said at least one data base from said data index means, online memory cache means and all other outside parties except during batch process of uploading pre-designated and fully-approved requests for medical data.

31. The system of claim 30 further including interface engine means enabling a search agent means to index said at least one data base of medical data.

32. The system of claim 1 further including means for billing said requesting party for a charge related to access to the medical data.

33. The system of claim 1 further including online memory cache means and means for delivering medical data to a requesting party including means for transmitting requested medical data held in digital form to said online memory cache means.

34. The system of claim 33 wherein said online memory cache means includes a firewall limiting access to said memory cache means exclusively to authorized users.

35. The system of claim 33 further including means for producing an indicia that said requested medical data have been received in said online memory cache means and are being held there for download by said requesting party.

36. The system of claim 34 further including means for said requesting party to enter through said firewall and download said medical data from said memory cache means.

37. The system of claim 1 including means for delivering medical data to a requesting party.

38. The system of claim 37 further including means for informing said requesting party when medical data is in a non-digital form and the mode of available delivery.

39. The system of claim 1 further including means for encrypting all communications within the system.

40. The system of claim 1 further including security log means for retaining an audit trail with regard to all of the communications within said system.

41. The system of claim 1 further including public portions, and comprising means for allowing parties to advertise in said public portions of said system.

42. A method of controlling access to medical data in a medical data base comprising:
  (a) maintaining at least one data base including medical data individually relating to each of a plurality of patients,
  (b) identifying medical data for each of said patients with indicia indicative of conditions required for access to said medical data,
  (c) selectively introducing requests for access to said data through an interconnected computer input terminal,
  (d) comparing said requests with said conditions; and, when said requests fail to comply with said conditions, automatically denying access to said data.

43. The method of claim 42 further including a step of authenticating identities of parties making said requests.

44. The method of claim 43 further includes the step of rejecting requests for information concerning medical records by any party without the prior authorization of the patient about whom such records pertain.

45. The method of claim 42 further including the step of tentatively identifying records fulfilling criteria specified in said requests for medical data.

46. The method of claim 45 further including a step of authenticating identities of said patients.

47. The method of claim 42 further including steps of requesting said medical data and indicating what part of said data is desired by said requesting party.

48. The method of claim 42 further including steps of requesting access to said medical records and indicating a reason said records are being requested.

49. The method of claim 42 including a step of ensuring that records fulfilling said requests include data symbolic of patient identities.

50. The method of claim 49 wherein said step of identifying records fulfilling said requests further include data symbolic of medical symptoms or reason for patient visit.

51. The method of claim 49 wherein said step of identifying records fulfilling said requests further include data symbolic of types of diagnostic tests performed.

52. The method of claim 51 wherein said step of identifying records fulfilling said requests further include data symbolic of the attributes, levels or findings indicated within said diagnostic tests.

53. The method of claim 49 wherein said step of identifying records fulfilling said requests further include data symbolic of modes of treatment or medical services rendered.

54. The method of claim 49 wherein said step of identifying records fulfilling said requests further include data symbolic of the ancillary services rendered.

55. The method of claim 49 wherein said step of identifying records fulfilling said requests further include data symbolic of attending physician identity.

56. The method of claim 49 wherein said step of identifying records fulfilling said requests further include data symbolic of date of care.

57. The method of claim 42 wherein said step of selectively introducing requests for access to said medical data includes a step of indicating a "standing order" that will automatically initiate an attempt to retrieve certain predetermined types of medical data under specific pre-specified circumstances.

58. The method of claim 42 wherein said conditions required for accessing said medical data include a step of indicating names of each party who's permission must be obtained prior to release of said medical data.

59. The method of claim 58 wherein said conditions required for accessing said medical data include an indication of the charge that will be assessed by the holder of such medical data for the part, or in the form, specified by the requesting party.

60. The method of claim 58 wherein said conditions for accessing said medical data include a step of indicating the time following the receipt of all approvals that will be required for the delivery of such medical data to the requesting party.

61. The method of claim 42 wherein maintaining said at least one data base includes maintaining a firewall limiting access to searching said data base solely to those parties who are authorized to do so.

62. The method of claim 42 further including providing a data index, and wherein identifying medical data fulfilling criteria specified in a request includes a step of producing an indicia of the degree to which data listed in said data index match said criteria specified in said request.

63. The method of claim 42 including a step of providing for a patient to grant permission to release of such medical data.

64. The method of claim 63 wherein said step of identifying medical data includes a step of billing for access to said medical data.

65. The method of claim 63 wherein said step of providing for a patient to grant permission includes data symbolic of the identity of said patient and data symbolic of a preferred means for contacting said patient to request access to and to release of said patient's medical data.

66. The method of claim 64 wherein said step of providing for a patient to grant permission includes providing data symbolic of rules to be followed in the event time elapses before said permission is granted in the case of pre-determined types of requests for said medical data.

67. The method of claim 42 further including a step of identifying a party requesting access to said medical data.

68. The method of claim 67 further including a step of authenticating identity of each party with a right of approval to release of said medical data.

69. The method of claim 68 further including a step of producing an indicia that all required approvals for release of said medical data have been secured.

70. The method of claim 69 further including a step of producing an indicia of approvals required for release of said medical data that have not been secured, or that have been specifically declined.

71. The method of claim 61 further including steps of providing a data index and online memory cache, and physically disconnecting said at least one data base from said data index, said online memory cache and all other outside parties except during batch process of uploading pre-designated and fully-approved requests for medical data.

72. The method of claim 71 further including a step of providing an interface engine for search agent means to index said at least one data base of medical data.

73. The method of claim 42 further including a step of billing a requesting party for a charge related to delivery of medical data.

74. The method of claim 42 further including steps of providing an online memory cache and delivering medical data to a requesting party and transmitting records in digital form to said online memory cache.

75. The method of claim 72 further including providing a firewall limiting access to said memory cache exclusively to authorized users.

76. The method of claim 72 further including a step of producing an indicia that requested medical data have been received in said online memory cache and are being held there for download by a requesting party.

77. The method of claim 75 further including a step of permitting a properly credentialed requesting party to enter through said firewall and download said medical data from said memory cache.

78. The method of claim 42 including a step of delivering records to the requesting party.

79. The method of claim 78 further including a step of informing a requesting party when medical data is in a non-digital form and the mode of such delivery.

80. The method of claim 42 further including a step of encrypting selected communications within said system.

81. The method of claim 42 further including a step of creating a security log and retaining an audit trail with regard to all of the communications between parties using said system.

\* \* \* \* \*